(12) United States Patent
Kaufhold et al.

(10) Patent No.: US 7,783,089 B2
(45) Date of Patent: Aug. 24, 2010

(54) METHOD AND APPARATUS FOR PROVIDING MAMMOGRAPHIC IMAGE METRICS TO A CLINICIAN

(75) Inventors: John P. Kaufhold, Altamont, NY (US); Bernhard E. H. Claus, Niskayuna, NY (US); Jeffrey W. Eberhard, Albany, NY (US)

(73) Assignee: General Electric Company, Niskayuna, NY (US)

( * ) Notice: Subject to any disclaimer, the term of this patent is extended or adjusted under 35 U.S.C. 154(b) by 1705 days.

(21) Appl. No.: 10/063,353

(22) Filed: Apr. 15, 2002

(65) Prior Publication Data

US 2003/0194115 A1    Oct. 16, 2003

(51) Int. Cl.
G06K 9/00 (2006.01)
(52) U.S. Cl. .................. 382/128; 382/130; 382/131; 382/132; 600/407; 600/408; 600/410
(58) Field of Classification Search .................. 600/407, 600/408, 410; 128/925, 920, 922; 382/128, 382/130, 133, 131, 132
See application file for complete search history.

(56) References Cited

U.S. PATENT DOCUMENTS

| | | |
|---|---|---|
| 3,971,950 A | 7/1976 | Evans et al. |
| 4,407,163 A | 10/1983 | Hundt et al. |
| 4,509,368 A | 4/1985 | Whitting et al. |
| 4,543,959 A | 10/1985 | Sepponen |
| 4,936,291 A | 6/1990 | Forssmann et al. |
| 5,235,510 A | 8/1993 | Yamada et al. |
| 5,361,767 A | 11/1994 | Yukov |
| 5,474,072 A | 12/1995 | Shmulewitz |
| 5,479,927 A | 1/1996 | Shmulewitz |
| 5,603,326 A | 2/1997 | Richter |
| 5,630,426 A | 5/1997 | Eggers et al. |
| 5,640,956 A | 6/1997 | Getzinger et al. |
| 5,660,185 A | 8/1997 | Shmulewitz et al. |
| 5,664,573 A | 9/1997 | Shmulewitz |
| 5,735,264 A | 4/1998 | Siczek et al. |

(Continued)

FOREIGN PATENT DOCUMENTS

JP    08-186762 A    7/1996

(Continued)

OTHER PUBLICATIONS

A. Thomas Stavros et al.: "Solid Breast Nodules: Use of Sonography to Distinguish between Benign and Malignant Lesions," Radiology, Jul. 1995, pp. 123-134, vol. 196, No. 1, Englewood, CO.

(Continued)

*Primary Examiner*—Brian Casler
*Assistant Examiner*—Baisakhi Roy
(74) *Attorney, Agent, or Firm*—Fletcher Yoder PC

(57) ABSTRACT

At least one metric for a mammographic image is computed by a workstation, and provided on a workstation display along with the mammographic image. A clinician can select one or more different metrics to be computed for an image, as well as where they are to be shown and the manner in which they are to be shown on the display. Speech (may also be an audible sound which is not speech) may also be used in the workstation to audibly provide metrics information to the clinician.

21 Claims, 10 Drawing Sheets

U.S. PATENT DOCUMENTS

| | | | |
|---|---|---|---|
| 5,776,062 | A | 7/1998 | Nields |
| 5,803,082 | A | 9/1998 | Stapleton et al. |
| 5,810,742 | A | 9/1998 | Pearlman |
| 5,815,591 | A | 9/1998 | Roehrig et al. |
| 5,820,552 | A | 10/1998 | Crosby et al. |
| 5,828,774 | A | 10/1998 | Wang |
| 5,840,022 | A | 11/1998 | Richter |
| 5,851,180 | A | 12/1998 | Crosby et al. |
| 5,855,554 | A | 1/1999 | Schneider et al. |
| 5,872,828 | A | 2/1999 | Niklason et al. |
| 5,938,613 | A | 8/1999 | Shmulewitz |
| 5,983,123 | A | 11/1999 | Shmulewitz |
| 5,984,870 | A | 11/1999 | Giger et al. |
| 5,999,639 | A | 12/1999 | Rogers et al. |
| 6,058,322 | A * | 5/2000 | Nishikawa et al. .......... 600/408 |
| 6,180,943 | B1 | 1/2001 | Lange |
| 6,678,462 | B1 | 1/2004 | Chihara |

FOREIGN PATENT DOCUMENTS

| | | | |
|---|---|---|---|
| JP | 8-336524 | A | 12/1996 |
| WO | 9909887 | A | 3/1999 |
| WO | 0013134 | A | 3/2000 |

OTHER PUBLICATIONS

Thomas M. Kolb et al.: "Occult Cancer in Women with Dense Breasts: Detection with Screening US-Diagnostic Yield and Tumor Characteristics," Radiology, Apr. 1998, pp. 191-199, vol. 207, No. 1.

Daniel B. Kopans et al.: "Development and Clinical Evaluation of Tomosynthesis for Digital Mammography; Technical and Cost Proposal," Clinical Translational Research Award, Department of Defense Breast Cancer Research Program, Nov. 19, 1997, pp. 1-54.

Nico Karssemeijer: "Computer-Aided Detection and Interpretation in Mammography," pp. 243-252.

Nico Karssemeijer et al.: "Detection of Stellate Distortions in Mammograms," IEEE Transactions on Medical Imaging, Oct. 1996, pp. 611-619, vol. 15, No. 5, IEEE.

Ioanna Christoyianni et al.: "Fast Detection of Masses in Computer-Aided Mammography," IEEE Signal Processing Magazine, Jan. 2000, pp. 54-64.

Celia Byrne et al.: "Mammographic Features and Breast Cancer Risk: Effects with Time, Age, and Menopause Status," Journal of the National Cancer Institute, Nov. 1, 1995, pp. 1622-1629, vol. 87, No. 21.

Milan Sonka et al.: "Computer-Aided Diagnosis in Mammography," Handbook of Medical Imaging—vol. 2. Medical Image Processing and Analysis, pp. 915-958, Spie Press, Bellingham, Washington.

Matthew A. Kupinski et al.: "Feature Selection and Classifiers for the Computerized Detection of Mass Lesions in Digital Mammography," IEEE Int. Conf. On Neural Nets, 1997, pp. 2460-2463, IEEE.

Shuk-Mei Lai et al.: "On Techniques for Detecting Circumscribed Masses in Mammograms," IEEE Transactions on Medical Imaging, Dec. 1989, pp. 377-386, vol. 8, No. 4, IEEE.

Marios A. Gavrielides et al.: "Segmentation of Suspicious Clustered Microcalcifications in Mammograms," Med. Phys., Jan. 2000, pp. 13-22, vol. 27, No. 1, Am. Assoc. Phys. Med.

Wei Zhang et al.: "Optimally Weighted Wavelet Transform Based on Supervised Training for Detection of Microcalcifications in Digital Mammograms," Med. Phys. Jun. 1998, pp. 949-956, vol. 25, No. 6, Am. Assoc. Phys. Med.

Berkman Sahiner et al.: "Computerized Characterization of Masses on Mammograms: The Rubber Band Straightening Transform and Texture Analysis," Med. Phys. Apr. 1998, pp. 516-526, vol. 25, No. 4, Am. Assoc. Phys. Med.

Zhimin Huo et al.: "Computerized Analysis of Mammographic Parenchymal Patterns for Breast Cancer Risk Assessment: Feature Selection," Med. Phys., Jan. 2000, pp. 4-12, vol. 27, No. 1, Am. Assoc. Phys. Med.

Datong Wei et al.: "Classification of Mass and Normal Breast Tissue on Digital Mammograms: Multiresolution Texture Analysis," Med. Phys. Sep. 1995, pp. 1501-1513, vol. 22, No. 9, Am. Assoc. Phys. Med.

John J. Heine et al.: "Multiresolution Statistical Analysis of High-Resolution Digital Mammograms," IEEE Transactions on Medical Imaging, Oct. 1997, pp. 503-515, vol. 16, No. 5, IEEE.

Wouter J. H. Veldkamp et al.: Normalization of Local Contrast in Mammograms, IEEE Transaction on Medical Imaging, Jul. 2000, pp. 731-738, vol. 19, No. 7, IEEE.

Wei Qian et al.: "Tree Structured Wavelet Transform Segmentation of Microcalcifications in Digital Mammography," Med. Phys., Aug. 1995, pp. 1247-1254, vol. 22, No. 8, Am. Assoc. Phys. Med.

Highnam et al.: "Mammographic Image Analysis," 1999, pp. 39-53, 191-223, 288, Kluwer Academic Publishers.

Duda et al.: "Pattern Classification," IWDM 2000, 5th International Workshop on Digital Mammography, 2001, pp. 161-199, Medical Physics Publishing, Madison, Wisconsin.

Laura M. Yarusso et al.: "Application of Computer-Aided Diagnosis to Full-Field Digital Mammography," IWDM 2000, 5th International Workshop on Digital Mammography, 2001, pp. 421-246, Medical Physics Publishing, Madison, Wisconsin.

Lihua Li et al.: "Hybrid Classification Method for False-Positive Reduction in CAD for Mass Detection," IWDM 2000, 5th International Workshop on Digital Mammography, pp. 272-279, Medical Physics Publishing, Madison, Wisconsin.

Robert P. Velthuizen: "Computer Description of Mammographic Masses," IWDM 2000, 5th International Workshop on Digital Mammography, pp. 395-401, Medical Physics Publishing, Madison, Wisconsin.

Armando Bazzani et al.: "Automatic Detection of Clustered Microcalcifications Using a Combined Method and an SVM Classifier," IWDM 2000, 5th International Workshop on Digital Mammography, pp. 161-167, Medical Physics Publishing, Madison, Wisconsin.

Yoshihiro Hagihara et al.: "Accurate Detection of Microcalcifications on Mammograms by Improvement of Morphological Processing," Hagihara et al., pp. 193-197.

M. Lanyi: "Diagnosis and Differential Diagnosis of Microcalcifications," pp. 44, 60, 61, 86, 95, 98-101, 110, 118-120, 192, 1987, Springer-Verlag.

Daniel B. Kopans: "The Positive Predictive Value of Mammography," AJR, Mar. 1992, pp. 521-526, vol. 158, American Roentgen Ray Society.

* cited by examiner

FIG. 1

Which Metrics Do You Want to Appear on the Mammogram Image?

- ● Microcalcifications
- ○ Overall Percent Glandular Composition
- ◐ Percent Glandular Distribution

[Next]

How Do You Want the Microcalcification Metrics to Appear on the Screen?

- ○ Histogram
- ● Geometric Shapes
- ◐ Voice Assisted

[Back] [Next]

Where Do You Want the Microcalcification Metrics to Appear on the Screen?

- ○ Separate from Mammo. Image on Corner of Screen
- ◉ Superimposed on Mammo. Image Near Region of Interest
- ◉ In Color

[Back] [Next]

How Do You Want the Percent Glandular Distribution Metrics to Appear on the Screen?

- ○ Histogram
- ◉ Geometric Shapes
- ○ Voice Assisted

[Back] [Next]

Where Do You Want the Percent Glandular Distribution Metrics to Appear on the Screen?

- ◉ Separate from Mammo. Image on Corner of Screen
- ○ Superimposed on Mammo. Image Near Region of Interest
- ◉ In Color

[Back] [Next]

510

— 35.3%

METHOD AND APPARATUS FOR PROVIDING MAMMOGRAPHIC IMAGE METRICS TO A CLINICIAN

STATEMENT REGARDING FEDERALLY SPONSORED RESEARCH & DEVELOPMENT

The government may have rights in this invention pursuant to subcontract 22287 issued from the Office of Naval Research/Henry M. Jackson Foundation.

BACKGROUND OF THE INVENTION

The present invention relates generally to providing computer-calculated metrics on a mammographic image to a clinician on soft copy display (e.g., monitor of a work station) to be used by the clinician for screening or diagnostic evaluation purposes.

Currently, clinicians, such as radiologists, perform diagnostic evaluation on mammographic images by looking for particular features within the mammographic images. That is, based on review of many different types of mammographic images, a clinician can determine whether or not a mammographic image has any potentially cancerous or suspicious regions.

Accordingly, due to the highly subjective nature of the mammographic image review process, it is possible that a clinician may incorrectly diagnose a mammographic image, which can lead to grave consequences for a patient due to the misdiagnosis.

BRIEF SUMMARY OF THE INVENTION

According to one aspect of the invention, there is provided an apparatus for use in mammographic analysis. The apparatus includes a workstation that has: a) an image receiving portion for receiving a digitized mammographic image, b) a computation portion for computing at least one metric related to the digitized mammographic image, and c) a display portion presenting to an operator the at least one metric. Throughout the discussion of the embodiments of the present invention, a "digitized" mammographic image may include either an x-ray film image (analog) that is converted to a digital image for display on a computer or workstation, or a mammographic image that is initially created in digital form (called FFDM in the literature, e.g.) and thereby can be inputted to a computer or workstation according to an embodiment of the invention without having to first digitize it.

According to another aspect of the invention, there is provided a method for analyzing a mammographic image. The method includes: a) receiving, by a workstation, a digitized mammographic image, b) computing, by the workstation, at least one metric related to the digitized mammographic image, and c) presenting to an operator, by way of the workstation, the at least one metric.

According to yet another aspect of the invention, there is provided a computer program product operable by a workstation for use in mammographic analysis. The computer program product includes: a) first program product code for receiving a digitized mammographic image, b) second program product code for computing at least one metric related to the digitized mammographic image, and c) third program product code for presenting to an operator, by way of the workstation, the at least one metric.

BRIEF DESCRIPTION OF THE DRAWINGS

The present invention will become more fully apparent from the following detailed description when read in conjunction with the accompanying drawings with like reference numerals indicating corresponding parts throughout, and wherein;

FIGS. 1-5 are diagrams of different menu screens that may be utilized in accordance with an embodiment of the invention;

DETAILED DESCRIPTION OF THE INVENTION

Figure 6:
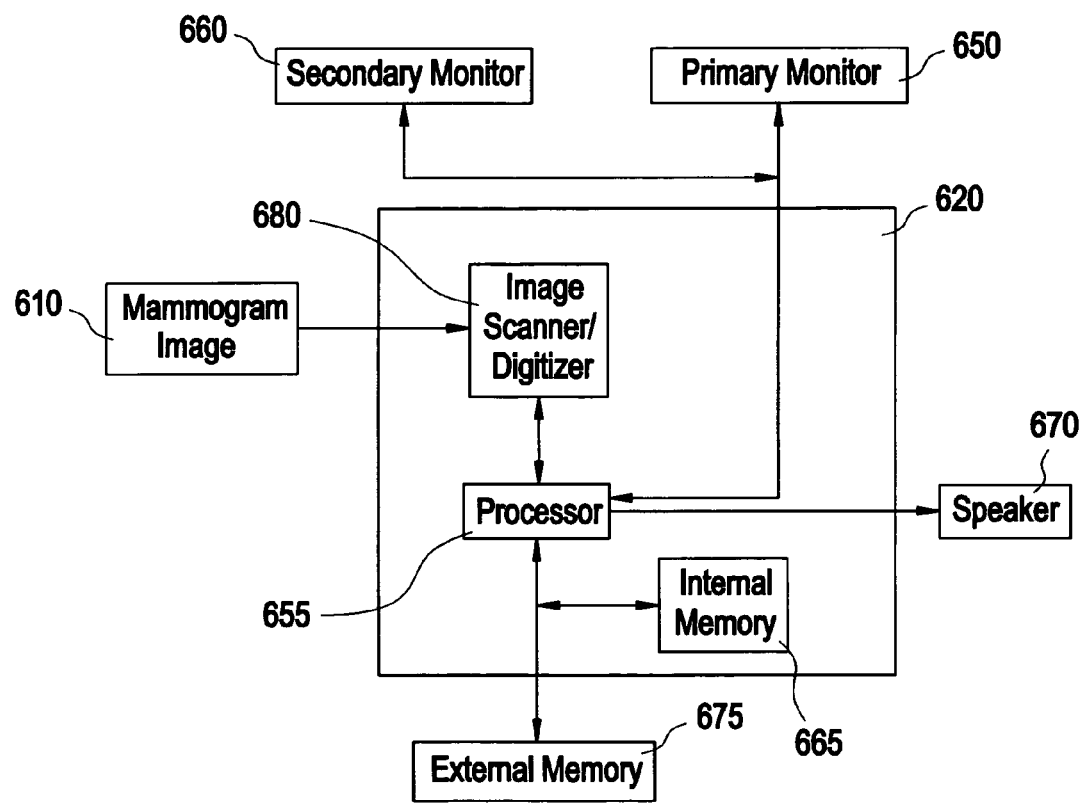
FIG. 6 is a block diagram of a work station that may be utilized in accordance with an embodiment of the invention.

A detailed description of the invention is provided herein, with reference to the accompanying drawings.

The present invention has been developed based on the premise that, given a mammographic image, it may be useful to present to a clinician certain quantitative metrics extracted from the image. For instance, it may be helpful to the clinician to have access to 1) the overall percent glandular composition or 2) the percentage glandular distribution, for instance. Further, after delineation of findings (microcalcifications, masses, or vessels, e.g.), either via computer-aided diagnosis (CAD) algorithms (automatic) or by hand-labeling (manual) or semi-automatic methods, it may be useful to the clinician to have at their disposal a summary of the quantitative measures of the findings.

For instance, a number of metrics may be useful for making decisions about the specific pathology associated with microcalcifications. Among others, metrics on the "clustering" of the microcalcifications, their size (both in the x-ray projection direction as well as in the image plane), and their shapes (both individually and as large or small groups), may be useful to the clinician for making screening or diagnosis decisions. Quantitative metrics on identified fibrous findings (e.g., suspicious masses, architectural distortion, etc.) may also be useful for making decisions about the pathology associated with them. For instance, masses often have dense centers, spicules, and ill-defined irregular margins. A metric related to each of these features on masses can be measured from image data and their presentation may also be useful to the clinician.

The present invention provides such quantitative metrics to the clinician in soft copy form via a workstation or personal computer. The present invention is directed to a way to allow a clinician to conveniently select, from a set of metrics, one or more metrics to be computed and displayed on a workstation display or screen, whereby the metrics are displayed along with a mammographic image. With such information provided to the clinician on the display or screen, the clinician can make relatively quick and definitive decisions with regards to a mammographic image, based on objective metrics provided by way of the present invention.

A brief description of the various metrics that have been described in the academic literature is provided below. These metrics are based on academic studies, and, to the best knowledge of the inventors of this application, are not being utilized by clinicians performing mainstream mammographic screening. Furthermore, these academic studies do not discuss, at least not in any detail, the manner in which such metrics can be made available to a clinician in a convenient manner so that the clinician can make a proper diagnosis of a mammographic image.

The present invention provides a convenient way, via a workstation or a personal computer, for the clinician to utilize one or more different metrics in their diagnosis, screening and analysis of mammographic images. In that respect, the present invention marries the academic world of mammographic image analysis with the "real" world of mammographic image analysis currently performed by clinicians.

In a book entitled "Mammographic Image Analysis", published by Kluwer Academic Publishers, 1999, the authors Highnam and Brady present one approach to bridging the gap between underlying breast anatomy and imaging physics which allows computation of a metric for what they term "interesting tissue" which means loosely a measure of the total amount of both glandular and potentially cancerous tissue in a given x-ray impinging on an x-ray detector pixel or film-screen location. From such an image, an overall percent glandular composition can be measured. In this book, a great deal of development is devoted to describing a specific approach to estimating the height (i.e., thickness) of "interesting tissue", but there is no meaningful development of how this information can be presented to a radiologist or clinician, specifically.

A number of other related metrics have been proposed in the literature for percent glandular composition estimation, including planimeter approaches, software approaches, and calibration approaches. Planimeter approaches are described in a report by C. Byrne et al., entitled "Mammographic Features and Breast Cancer Risk: Effects With Time, Age, and Menopause Status", published in the Journal of the National Cancer Institute, Vol. 87, No. 21, Nov. 1, 1995. Software approaches are described in the Highnam and Brady book discussed above. Calibration approaches are described in an article by J. Kaufhold et al., entitled "Tissue Composition Determination in Digital Mammography", published in the Proceedings of the Annual Meeting of the Radiological Society of North America, Nov. 25-30, 2001, Chicago, Ill.

A number of quantitative metrics are available to label pathologic mammographic features in images. These quantitative metrics have been described in the literature. Because many articles describe only a subset of these quantitative metrics, and this subset may belong to a number of classes of quantitative metrics utilized in the present invention for implementation on a personal computer or workstation, some of the relevant literature is listed here with a brief discussion of some of the metrics which can be incorporated into the presentation frameworks described herein. See, for example, the following references: a) M. A. Gavrielides et al., "Segmentation of Suspicious Clustered Microcalifications in Mammograms", published in Med. Phys. 27 (1), January 2000; b) W. Zhang et al., "Optimally Weighted Wavelet Transform Based on Supervised Training for Detection of Microcalcifications in Digital Mammograms", published in Med. Phys. 25(6), June 1998; c) B. Sahiner et al., "Computerized Characterization of Masses on Mammograms: The Rubber Band Straightening Transform and Texture Analysis", published in Med. Phys. 25(4), April 1998; d) Z. Huo et al., "Computerized Analysis of Mammographic Parenchymal Patterns for Breast Cancer Risk Assessment: Feature Selection", published in Med. Phys. 27(1), January 2000; e) D. Wei et al., "Classification of Mass and Normal Breast Tissue on Digital Mammograms: Multiresolution Texture Analysis", published in Med. Phys. 22(9), September, 1995; f) J. J. Heine et al., "Multiresolution Statistical Analysis of High-Resolution Digital Mammograms", published in IEEE Transactions on Medical Imaging, Vol. 16, No. 5, October, 1997; g) H. Veldkamp et al., "Normalization of Local Contrast in Mammograms", published in IEEE Transactions on Medical Imaging, vol. 19, No. 7, July 2000; h) W. Qian et al., "Tree Structured Wavelet Transform Segmentation of Microcalcifications in Digital Mammography", published in Med. Phys. 22(8), August, 1995; i) M. Sonka et al., "Handbook of Medical Imaging, Volume 2, Medical Image Processing and Analysis", published by SPIE Press, 2000; j) S-M. Lai et al.; "On Techniques for Detecting Circumscribed Masses in Mammograms", published in IEEE Transactions on Medical Imaging, Vol. 8, No. 4, December, 1989; and k) M. A. Kupinski and M. L. Giger, "Feature Selection and Classifiers for the Computerized Detection of Mass Lesions in Digital Mammography", published in Proceedings of the IEEE International Conference on Neural Nets, 1997.

Some of the references listed above contain methods to extract the quantitative information for specific quantitative metrics and some contain a definition of a clinically useful related metric, and some both. As for the case of percent glandular composition, the relevant papers devote a great deal of development to the definition of such metrics, but very little, if any, development of how this information might be presented to the clinician. The present invention is directed to a convenient way of computing that information and presenting that information to the clinician.

Similarly, microcalcification metrics are defined in detail in some of the literature, but a means for their presentation to the clinician is usually left largely undeveloped or not discussed at all. For an example of a microcalcification cluster shape metric, see the Highnam and Brady book or M. Lanyi, "Diagnosis and Differential Diagnosis of Microcalcifications", Springer-Verlag, 1987. For an example of metrics on individual microcalcifications, see the Highnam and Brady book; or E. A. Sickles, "Management of Probably Benign Breast Lesions", Radiol. Clin. North Am., 33(3), 1995; or I. M. Freundlich et al., "Computer-Assisted Analysis of Mammographic Clustered Calcifications", Clinical Radiology, 40:296-298, 1989. For a number of quantitative metrics on fibrous findings (suspicious masses, e.g.), see N. Karssenmeijer and G. M. te Brake, "Detection of Stellate Distortions in Mammograms", IEEE Transactions on Medical Imaging, 15: 611-619, 1993; or the B. Sahiner et al. article; or the D. Wei et al. article.

Some computer-assisted mammography tools are commercially available, and some computer-assisted mammography papers are available in the literature. For example, see I. Christoyianni et al., "Fast Detection of Masses in Computer-Aided Mammography", published in IEEE Signal Processing Magazine, pages 54-64, January 200; or see M. I. Giger et al., "Computer-Aided Diagnosis in Mammography, in Handbook of Medical Imaging", Vol. 2: Medial Image Processing and Analysis, edited by M. Sonka and J. M. Fitzpatrick, pages 915-1004, published by SPIE Press, 2000. These products and papers usually focus on what information is most relevant, the comparative performance of different metrics, or the definitions of metrics themselves. Beyond a means to indicate findings on a mammogram (with pointers such as triangles, arrows, circles, or other pointing region descriptors), very little in this literature is directed to utilizing workstation capabilities, or what potential approaches for presentation of this information may be valuable and efficient for clinical use.

In that regard, the present invention provides a method and apparatus for presenting quantitative information derived from mammographic images to the clinician. In the present invention, "quantitative information" will often be referred to using the general term "metric". A metric need not be a number, specifically, but will be some representation of a measured mammographic feature (e.g., the set of words, fatty, possibly cancerous, suspicious, etc. could describe the range of values for a given metric defined as "impression").

Global breast metric presentation examples are provided below as one example of how such metrics can be provided to a clinician by way of a personal computer or workstation, to thereby allow the clinician to readily analyze and perform a diagnosis of a mammographic image.

One metric which will likely become more important to clinical mammographers in the near future as a risk and evaluation confidence assessment tool is the overall percent glandular composition of a breast. However the manner in which the percent glandular metric is calculated, there are a number of ways to present it to the clinician by way of the present invention. Likewise, other global metrics may be available to the workstation according to the invention, which may also be presented on a display for convenient review by the clinician. For instance, the breast area, the compressed breast height, the breast shape, and a summary metric for the spatial distribution of breast density, are all examples of auxiliary metrics that may also be presented using presentation approaches according to embodiments of the invention as described below.

Figure 8:
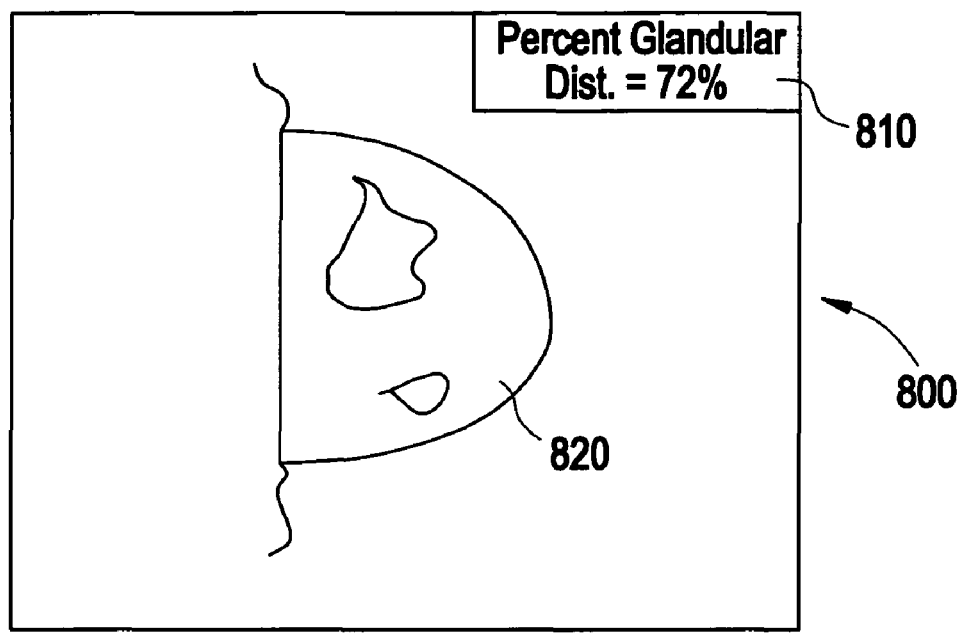
FIG. 8 is a diagram of a mammographic image displayed on a workstation display along with metric information, according to an embodiment of the invention.

If a global metric for the breast view is calculated, however it is calculated, it may be displayed on the workstation according to an embodiment of the invention with an appropriate label in a region of the screen where it will not distract the clinician while also being easily accessible. In this configuration, the monitor or display of the workstation may have a first region for displaying the mammographic image, and a second region for displaying the metric or metrics obtained from the mammographic image. FIG. 8 shows a global metric 810 describing the percent glandular composition of a breast that is displayed in a corner of a workstation screen 800. A mammographic image 820 also is displayed on the workstation screen 800 as shown in FIG. 8.

According to an embodiment of the invention, a workstation may include speech synthesis software that is capable of using speech synthesis techniques to audibly describe a metric, such as a global breast metric, to the clinician. In the present invention, the term "speech" may include speech as well as non-speech audible sounds (e.g., beep sound, ping sound, predetermined tone or tones, etc.). For example, one potential means to communicate the density of the particular breast on the screen is for the workstation to "say", via speech synthesis software and applicable audible (audio) components (e.g., amplifier, speaker, headphones, etc.) known to those skilled in the art, "The overall percent glandular composition of this breast is 72%", for instance.

In an alternative configuration, some information related to the global metrics can be presented on a coarse scale but slightly finer than that described by a single global summary metric. For instance, one visual approach to displaying a global breast metric that is related to percent glandular composition is to display a smaller image of the breast in an unused region of the review workstation or on an auxiliary screen. This smaller image could be a subsampled mammogram without standard postprocessing for presentation purposes (thickness compensation or dynamic range management, e.g.), so as to preserve the "impression" of the raw mammogram to the clinician, but any alternative approach that achieves these goals is also possible.

Figure 9:
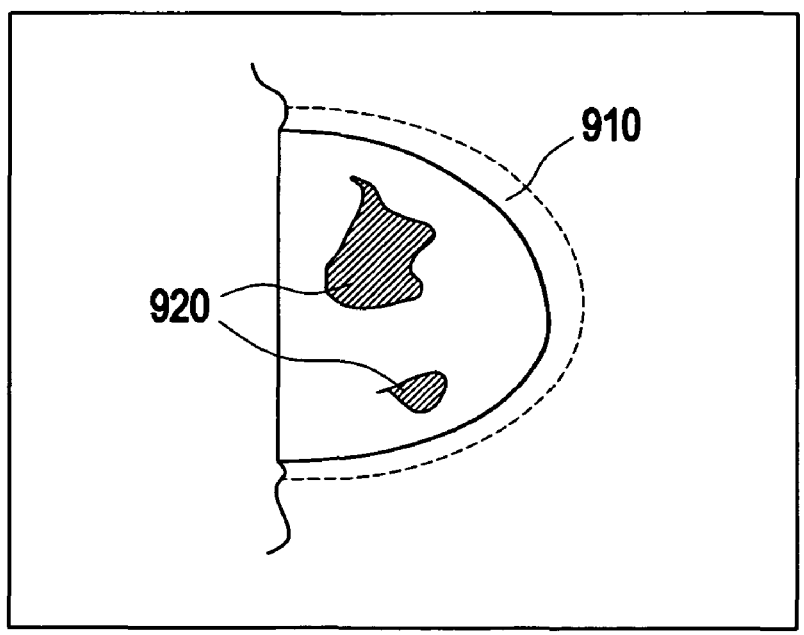
FIG. 9 is a diagram mammographic image displayed on a workstation display with various portions of the image being displayed with different color characteristics, according to an embodiment of the invention.

According to an embodiment of the invention, color coding may be utilized to display the metric information. For example, the coarse scale glandular composition impression can be aided via color-coding. FIG. 9 shows one implementation of a mammogram display on a workstation screen having color-coding, according to an embodiment of the invention. In FIG. 9, dense regions are shown in one color as indicated by regions 920 (e.g., red), and noncompressed breast regions are shown in a different color as indicated by region 910 (e.g., blue) on the black-and-white mammographic image.

Likewise, for a compressed breast height, instead of simply displaying a number, a diagrammatic version of the compressed breast may be displayed. This diagrammatic approach to separating thickness and density measurements/impressions may be especially useful for a workstation that can perform postprocessing steps so that structures in very dense regions of the breast are visible. These postprocessing steps, although allowing the clinician to "visually penetrate" dense regions, may also alter the overall "impression" of the breast to the radiologist. In this way, the radiologist can both penetrate dense regions of the breast as well as draw on their own experience with the densities of other breasts to develop a more complete "impression" of each breast.

Figure 10:
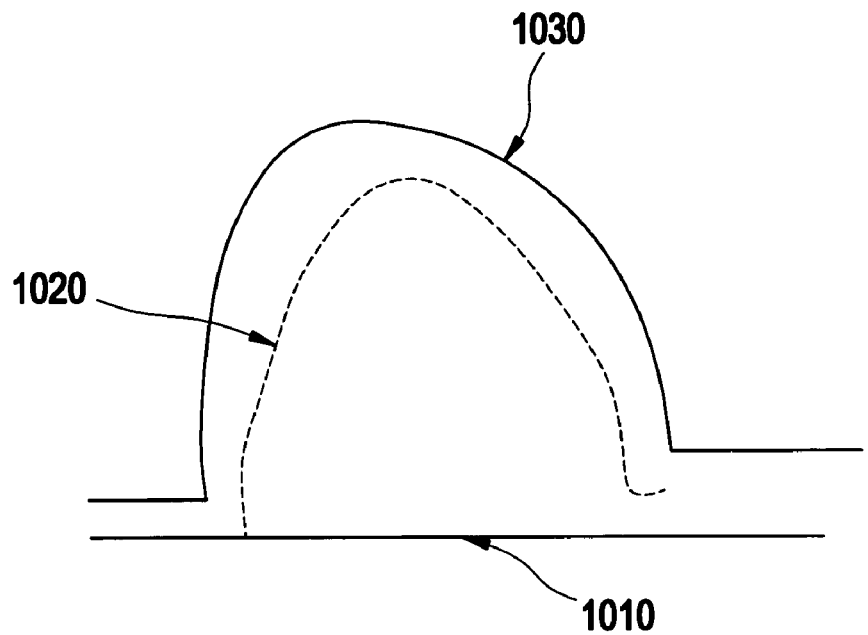
FIG. 10 is a diagram mammographic image displayed on a workstation display with various portions of the image being displayed with different contour characteristics, according to an embodiment of the invention.

Isocontours of percent glandular tissue or a contour delineating some other feature (such as the compressed breast region, which corresponds to the part of the breast in contact with the compression paddle during the examination) may also be useful and may also be displayed directly on the display of the breast on the review workstation screen. FIG. 10 provides an example of an intensity contour that delineates the skinline curve 1030, a specific percent glandular curve 1020, and a pectoral muscle 1010 on a patient breast, according to an embodiment of the invention. Breast implants can also be labeled similarly.

Figure 11:
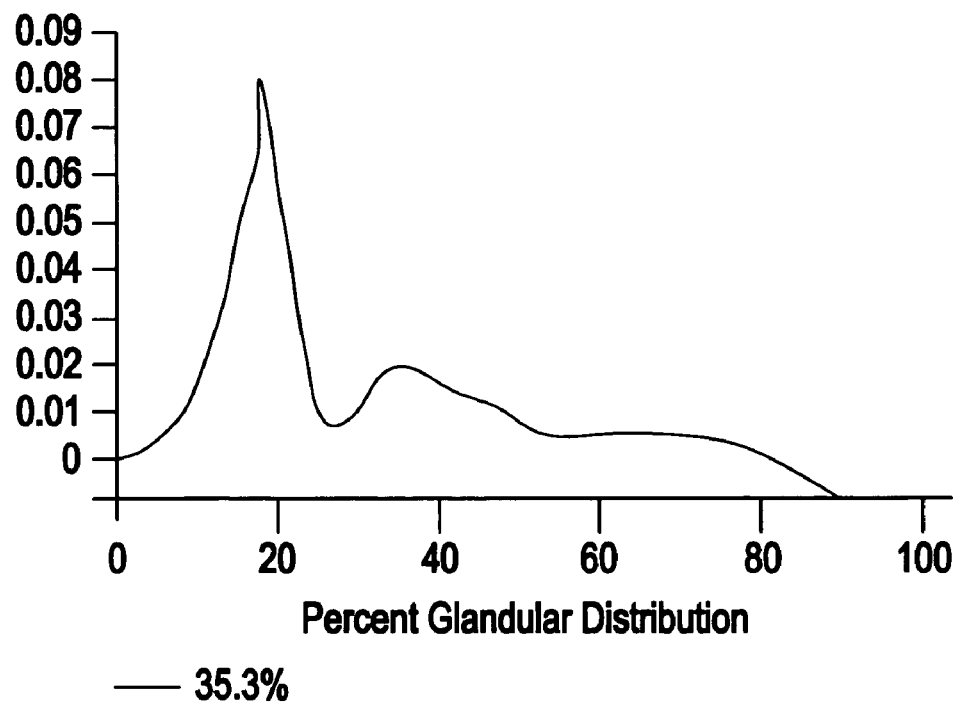
FIG. 11 is a histogram of a mammogram metric that is displayed by a workstation according to an embodiment of the invention.

FIG. 11 shows a histogram of the percent glandular breast composition that may be displayed on a workstation screen according to an embodiment of the invention. In FIG. 11, only the histogram is displayed, but it is possible to coordinate the color-coding of the constituent histogram bar heights with the color coding for a given density distribution or contour plot overlay displayed in some other part of the review workstation screen.

Another set of metrics that may be provided to a clinician using a workstation according to an embodiment of the present invention are metrics of microcalcifications. Microcalcifications are often the earliest indicators of breast cancer on a mammogram. The state of the art in mainstream medicine today may provide the clinician, through computer-assisted diagnosis techniques, with a region of interest marker (an arrow or circle, for instance) where the computer detects a suspicious cluster of microcalcifications. The present invention provides convenient ways to present this information, as well as derived quantitative information, to the clinician, by way of a personal computer or a workstation. The discussion below focuses on presenting quantitative metrics on microcalcification clusters as well as quantitative metrics on individual microcalcifications.

A microcalcification cluster may be described as a collection of more than some minimum number of microcalcifications occurring in a localized region on a mammogram. Understanding the structure of each cluster quantitatively is still an open topic in mammography research, and some of these metrics, when shown to be clinically relevant, can be incorporated into a review workstation according to an embodiment of the present invention for quantitative information presentation. There are described herein various approaches for quantifying microcalcification cluster metrics, but it is noted that many of the presentation tools described herein will be useful for presenting other related quantitative information to the clinician by way of a personal computer or a workstation according to the present invention.

Figure 12:
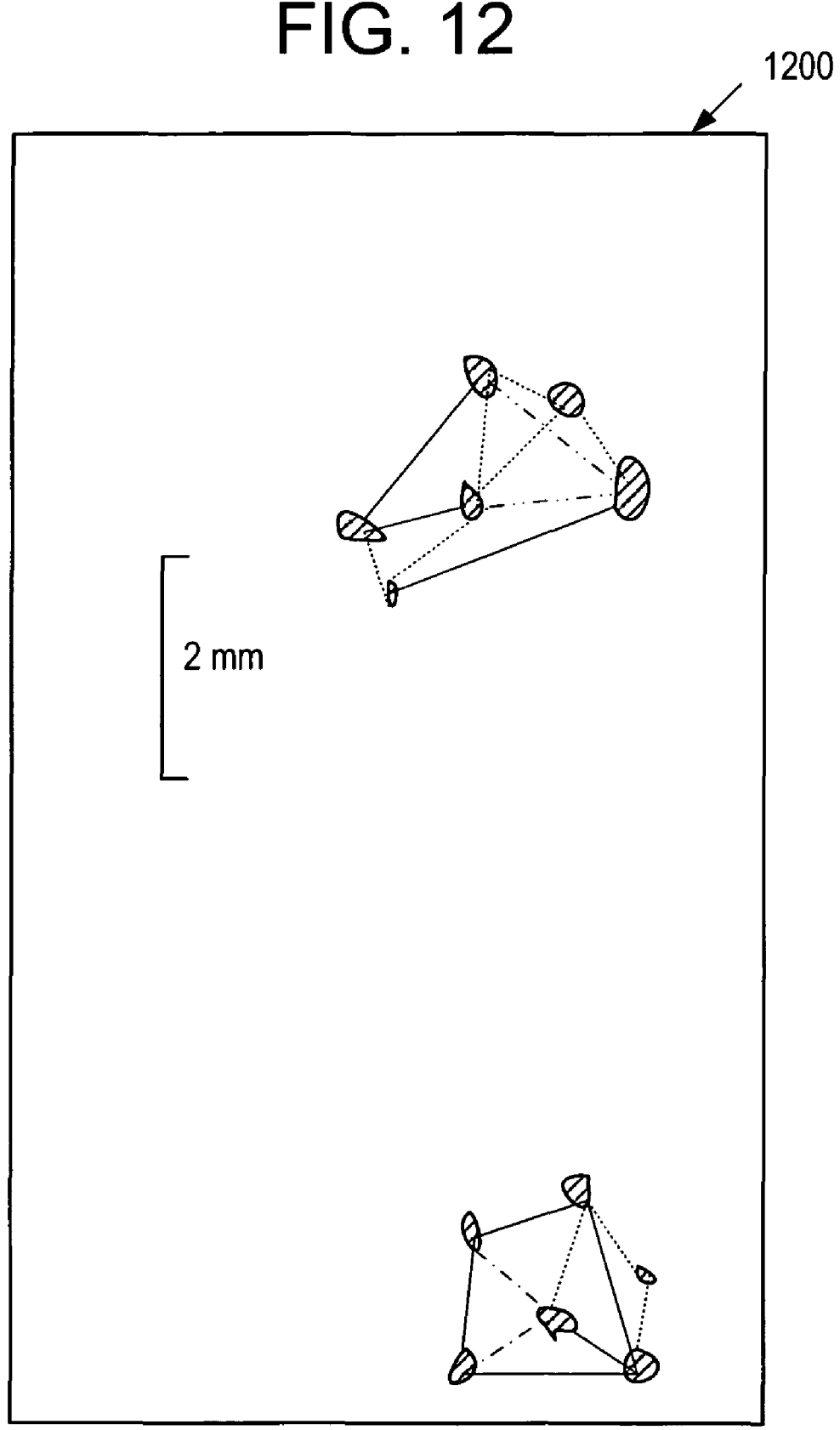
FIGS. 12-15 show a portion of a mammographic image that has microcalcification metrics displayed alongside microcalcifications, according to an embodiment of the invention.

One way to quantify a cluster's "span", which means loosely, the proximity of microcalcifications within the cluster "border", is to rank-order the distances between constituent microcalcification centers within the cluster. For instance, in FIG. 12, there are two clusters in the displayed zoom image. The rank-ordered distances between each individual microcalcification center and its closest, second closest, and third closest microcalcification neighbor's center are preferably labeled with different colors such as green, yellow, and red, respectively, or by different line types as shown in FIG. 12. These are microcalcification "connections". If there are two different connection color labels between two microcalcifications, the label precedence for display is green, yellow, then red, for example (or nondashed, semi-dashed, and dashed in the mammogram image 1200 shown in FIG. 12, for example). This is not the only way these microcalcification "connections" can be presented, however. Alternatively, the "connections" can be labeled with a number representing the actual distances between centers, or the color of the "connections", themselves can code an actual distance rather than a ranked proximity to other microcalcifications. Other ways of presenting microcalification metrics to a clinician by way of a workstation screen according to embodiments of the present invention may also be contemplated, without departing from the scope of the invention as described herein.

On an auxiliary monitor or on an unused region of the review workstation display screen, the microcalcification cluster can be represented as a graph, which in isolation from the background tissue may also be useful to the clinician. For instance, the relative locations of constituent microcalcifications in a microcalcification cluster can be represented by the graph defined by the microcalcification centers, their nearest neighbors, and connections to their nearest neighbors. The graph nodes can be represented by some symbol (a circle, e.g.), with area related to the actual measured size of the microcalcification. In addition, depending on the desired complexity, even the graph nodes can be color-coded or otherwise labeled with associated parameters, such as shape, for instance. In this way, the microcalcification cluster "skeleton" can, if desired, be visualized conveniently in isolation from the underlying and overlying tissue (in three dimensions, for example, for 3D breast images).

Another visualization of the microcalcification adjacency can be realized via a Voronoi diagram, where the centers of the individual microcalcifications comprising a cluster are separated by a bisecting line at a point equidistant to each pair of nearest microcalcifications. For an extended description of some cluster metrics and presentation approaches for clusters of point sets, see R. O. Duda and P. E. Hart, "Pattern Classification and Scene Analysis", published by John Wiley and Sons, 1973. Any of the approaches for cluster analysis described in Duda and Hart's book can be applied to microcalcification cluster analysis and presentation by way of a personal computer or workstation according to an embodiment of the present invention.

A convex hull is another approach for presentation of microcalcification cluster features, which can be utilized by way of an embodiment of the present invention. From the cluster's constituent microcalcification center points, a convex hull can be fitted which contains the segmented cluster completely. The overall "shape" of the entire cluster can be measured as well (using the microcalcification center location information, e.g.) and a number or collection of numbers can be used to describe the overall shape. The number or collection of numbers can then be displayed in some intuitive juxtaposition to the cluster or in some unused portion of the review workstation screen in a summary or exhaustive description format.

In addition, the number of individually identified microcalcifications within a cluster may be useful information to provide to a clinician by way of the present invention. That number can also be displayed in the same way as the shape information, either in juxtaposition to the clusters themselves, or in a summary form in an unused portion of the review workstation screen or on an auxiliary screen where they are both nondistracting and accessible.

If certain derived metrics can be used in conjunction with one another to describe a clinically relevant "type" of cluster, that information may also be displayed in juxtaposition to the cluster or in an unused portion of the review workstation screen. For instance, if the number of microcalcifications in a cluster is greater than a first threshold value, and its shape metric is less than a second threshold value, that cluster can be labeled "linear" and displayed to the clinician in that manner on a workstation screen (and/or presented to the clinician by way of an audible signal via speech synthesis software, if desired), which provides immediate value for the clinician In addition to metrics on the cluster itself, the cluster juxtaposition to other structures, such as ducts and/or blood vessels, may be included on the workstation screen and thereby provide the clinician with other valuable information. The ducts and/or blood vessels can be labeled with different colors or some other indicator on the workstation screen.

For microcalcification clusters, any subset of the available quantitative metrics that might be displayed for the clinician may also be a candidate for speech synthesis reporting. Instead of displaying all the quantitative metric information at various locations on the workstation screen, a system of synchronized reporting with a coordinated image labeling is also possible. For instance, as a circle is drawn around one of a number of microcalcification clusters on the review workstation screen, the workstation may report metrics on that particular cluster to the clinician via speech synthesis: "A non-suspicious microcalcification cluster of four microcalcifications in an elliptical shape." Then the circle around the first microcalcification cluster might disappear and then the circle would reappear around another of the microcalcification clusters and another appropriate message pertaining to the new cluster would be audibly reported to the clinician by way of a personal computer or workstation according to an embodiment of the present invention.

Like microcalcification clusters, metrics on individual microcalcifications may also be useful to the clinician, and can be provided to the clinician along with a mammographic image, by way of a personal computer or a workstation according to an embodiment of the invention. Some interesting features that may be useful to report to the clinician include size and shape measurements. For instance, from the detected microcalcification image, the number of pixels comprising one microcalcification is one way to measure its size in the image plane.

Figure 13:
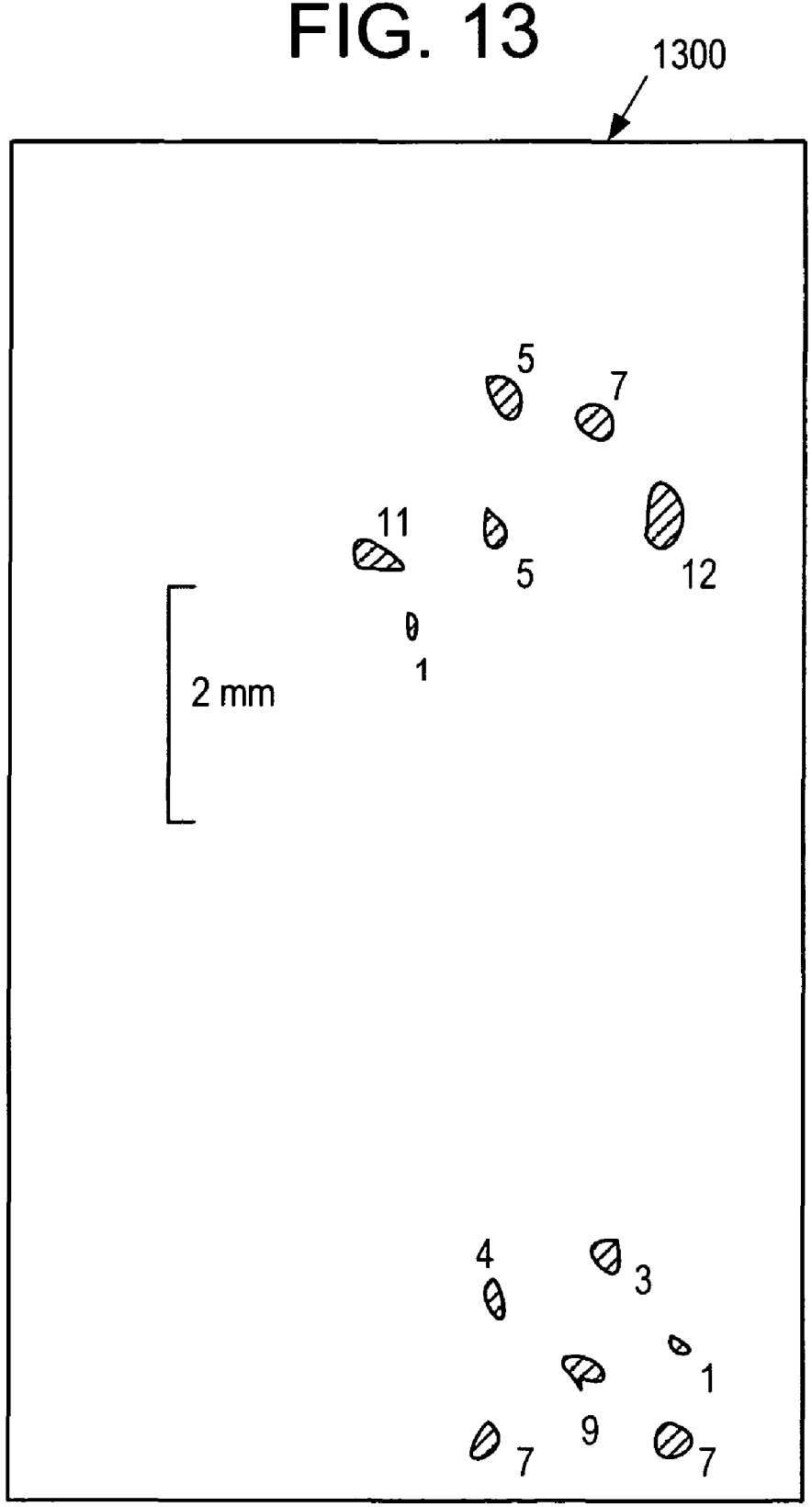

In FIG. 13, a blown-up portion of a mammography image 1300 shows microcalcifications that can be outlined in a different color than the rest of the mammographic image. The number of pixels comprising each microcalcification is juxtaposed near each microcalcification outline. Like the microcalcification cluster metric presentation described above, FIG. 13 shows only one approach to presenting this information to a clinician. These individual numbers can also be listed on the margin of the image or in an unused portion of the review workstation screen. They can be presented unsorted or sorted by size or some other clinically relevant metric.

Like the clusters, the individual metrics can be reported to the clinician via speech synthesis techniques. For instance, in a speech reporting mode, an arrow indicating a specific microcalcification might appear while the workstation reports audibly: "seventeen pixels". Then the arrow might disappear and reappear at another microcalcification and report its size. For individual microcalcifications, any combination of reporting and metric can be used. Other metrics which may be useful to report to the clinician, and which may be provided to the clinician by way of a workstation according to the invention, include, but are not limited to 1) projection in the z direction and 2) quantitative shape metrics.

Figure 14:
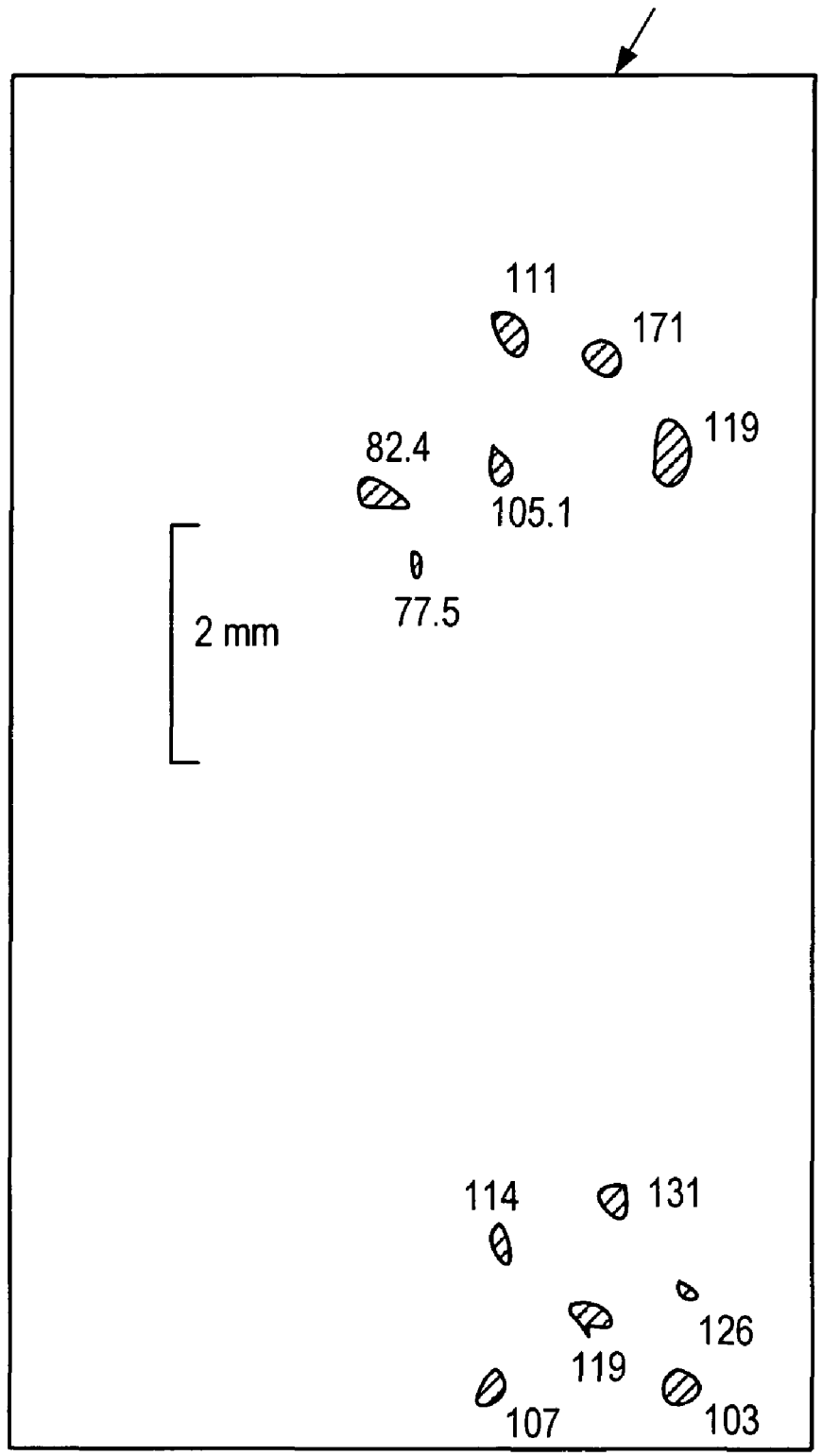

The projection in the z direction means that the excess intensity (and thus, thickness in the z direction) of a local intensity spike due to a microcalcification can be estimated. For instance, if the local region on the mammogram is filtered to remove the "low-pass" glandular tissue background in the log-count image domain, presumably all the excess intensity inside the microcalcification outline comes from the microcalcification itself. The peak excess intensity in this region allows estimation of the maximum thickness of the microcalcification in the z direction (z direction means the direction formed by the line connecting detector pixel to the anode focal spot). FIG. 14 shows an example of the z direction projection metric provided for a workstation image on a workstation screen 1400 according to an embodiment of the invention.

Figure 15:
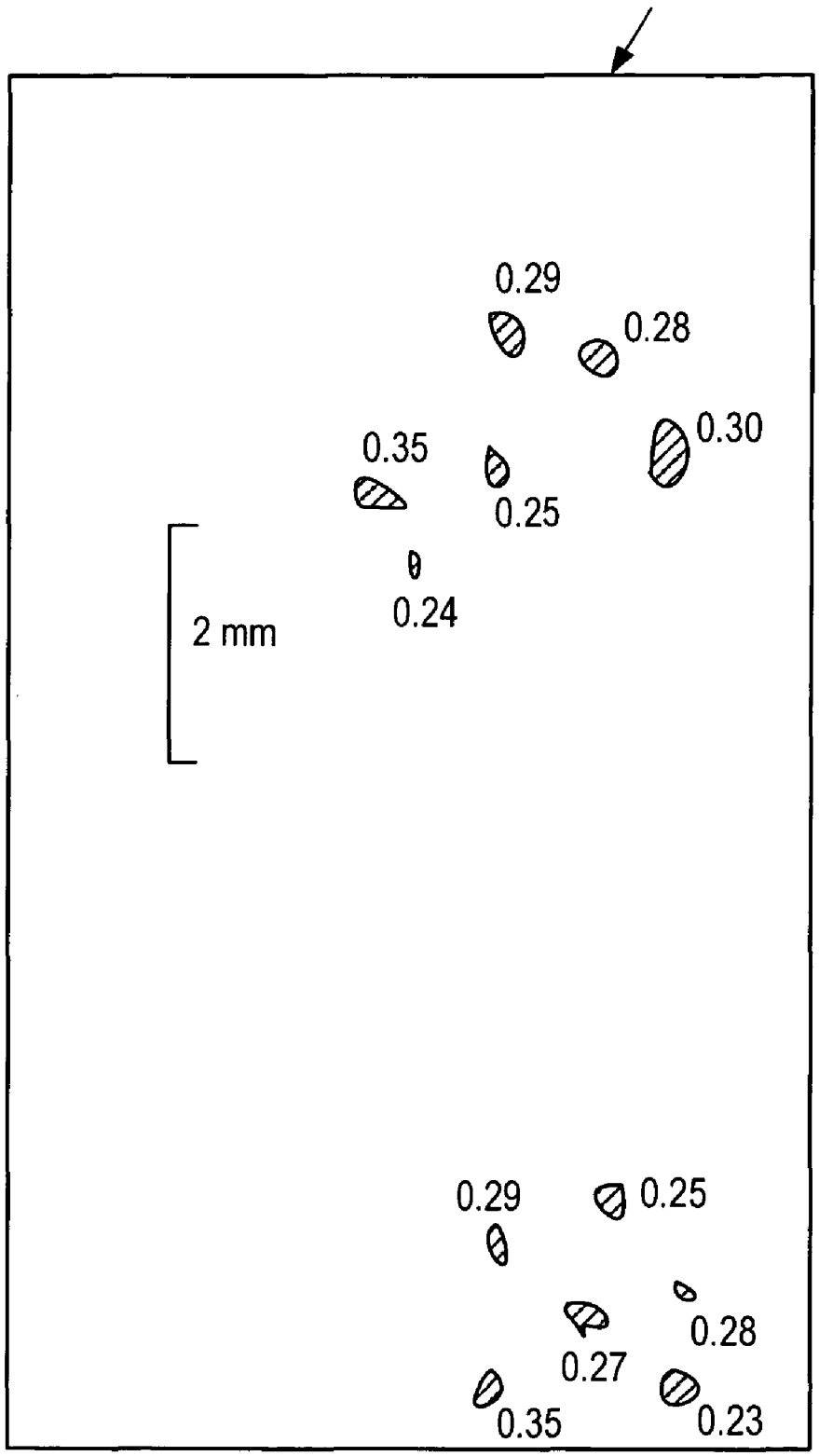

Shape metrics may include, among others, 1) the area-to-perimeter ratio or 2) an eccentricity metric for an ellipse fit to the outline of the microcalcification. An example of the area-to-perimeter ratio metric provided for a workstation on a workstation screen 1500 according to an embodiment of the invention is shown in FIG. 15.

For individual microcalcifications, a number of metrics useful to the clinician are made available for presentation to the clinician by way of a personal computer or a workstation according to an embodiment of the invention. The metrics may be presented in close juxtaposition to the outlined microcalcifications, themselves. There may be other ways to label these structures quantitatively, according to the present invention. For instance, the color used to highlight the microcalcifications that have metrics computed for them (and displayed on the display) can be any color, which may be an operator-selected color. The solid lines shown in the figures could alternatively be dashed lines or some other line type. Alternatively there may be shown no line at all, only the close juxtaposition of the metric.

As described for the microcalcification sizes, they may also be listed in summary or exhaustive form in the margin of the review workstation screen or some other accessible and non-distracting location. One summary form may be an average size with an estimate of size variability for a given cluster. Further, a synchronized microcalcification indicator and speech synthesis reporting tool can be used for presentation. For instance, as described above, an arrow indicator and whatever microcalcification metrics the clinician requests can be read out in a coordinated fashion. All of the above features are preferably selected by a clinician during an initial setup mode, whereby the clinician defines the metrics to be displayed and the manner that they are to be displayed on a workstation screen.

As for glandular composition, microcalcification clusters and individual microcalcification metrics, fibrous findings (e.g., suspicious mass) metrics may also be useful to the clinician for decision-making on a specific mammogram. Fibrous findings metrics may also be made available on a workstation display screen to a clinician, if the clinician chooses to review these types of metrics for a mammographic image. Again, during an initial setup mode, the clinician can elect to have such computed and displayed for a mammographic image.

Useful metrics for presentation to the clinician include, but are not limited to 1) a spiculation index, 2) a center density, 3) some metric for mass size, 4) some mass shape metric 5) some mass margin metric, describing whether the mass is circumscribed (smooth margin) or otherwise, or 6) some mass metric derived from all available mammogram information, including all mammographic metrics. These metrics require more involved calculations than the metrics previously described, but these are readily available in the literature. These other metrics can be computed and plotted by a workstation or personal computer according to the invention in a short period of time.

The present invention provides a way to compute and to present any subset or superset of metrics to the clinician. Like the microcalcification cluster or individual microcalcification metrics, the clinically useful mass metrics may include a collection of descriptive numbers and/or terms (words) that can be estimated from the mammogram image properties. Like the microcalcifications, these numbers and/or terms may be presented to the clinician in close juxtaposition to the identified mass, with or without some indicator (such as an arrow, circle, or other indicator). They may also be reported in some unused portion of the review workstation screen in either summary or exhaustive description form.

Like the microcalcification clusters and individual microcalcifications, a speech synthesis reporting tool may also be useful. Again, this reporting technique could include some indicator (such as an arrow, circle, or other indicator) which appears as the speech synthesis reports some appropriate message, such as: "this region contains a suspect DCIS-type triangular mass with a spiculation index of 0.7, a size of 1.2 cm, with irregular margins." The indicator could then index to the next mass and report the metrics for the indicated region.

As for the microcalcification clusters, an estimated outline of the mass can be displayed, either in a separate window in an unused portion of the review workstation screen, or overlaid on the mammogram. The margin of the displayed shape can again be color-coded depending on the characteristics of the margin of the mass, the shape can be filled (semi-transparently in the overlay display) in a color corresponding to some additional metric, e.g., estimated thickness of the mass.

The embodiments described above provide a number of ways that clinically relevant quantitative information may be presented to the clinician. The emphasis is on the way the information derived from the image is presented to the clinician, not on the specific calculation or identification of the metrics, themselves. In the previously-described embodiments, ways have been described to present quantitative information pertaining to 1) the overall glandular composition of the breast 2) microcalcification clusters 3) individual microcalcifications and 4) fibrous findings (e.g., suspicious masses). Of course, other metrics may be utilized with a personal computer or workstation in accordance with an embodiment of the invention.

There are some common themes to each of these presentation strategies described with respect to the different ways of displaying metrics in accordance with embodiments of the invention. These quantitative metrics include numerical, symbol, and/or word labels. In current mammography systems, some word labels are already used, such as "MLO" to describe the view. However, the use of words and labels for a large selection of quantitative metrics on mammographic image features is not believed to be used in mainstream radiology mammography workstations, to the best knowledge of the inventors of this application.

In the presentation of quantitative metrics in mammography workstations according to the present invention, quantitative metrics can be presented on a display in juxtaposition to the actual image features they describe. Such approaches include 1) presenting the quantitative metric(s) in close juxtaposition to the image feature described by the quantitative metric 2) presenting the quantitative metric(s) in an "unused" region of the review workstation (such as the margin or the screen area between the skinline and the workstation monitor border or screen window controls; another possible approach is to include an auxiliary display device used primarily for reporting quantitative metrics), 3) presenting the quantitative metrics as a color, shape, area, symbol, linetype or brightness-coded structure (such as the rank-ordered microcalcification "connection" example), or 4) a coordinated visual indicator and audio (speech, e.g.) signal approach where the mammographic feature described by the audio signal is indicated while the audio signal is presented to the radiologist.

The quantitative metric presentation approaches described with reference to the present invention are typically influenced by user preferences. For instance, some clinicians may make decisions based mostly on one type of information for which some or all of the quantitative metrics are useful aids. Other clinicians may want to use none of the quantitative metrics in decision-making, similar to the standard practice in radiology in mainstream medicine today. The user preferences define much of the interface between the radiologist and review workstation. The quantitative metrics are subject to coordination according to the selected user preferences. For instance, some clinicians might choose to have the percent glandular composition, or some related metric, like a histogram, presented in the upper left hand corner of the mammograms they screen or diagnose. That same radiologist may prefer to have the mass metrics, when available, reported to them via speech) synthesis, and may want to see only microcalcification cluster information reported in close juxtaposition to each microcalcification and no quantitative information on individual microcalcifications. Thus, the presentation approaches described herein form a substrate from which the user preference selections can be used to define a richer screening or diagnostic environment for the clinician.

According to an embodiment of the present invention, display of quantitative metrics for single clusters, individual microcalcifications, individual masses, can optionally be controlled by identification with or proximity to the mouse cursor on the screen. Likewise, a touch screen, in place of, or in conjunction with, a mouse cursor can also be used. Such an approach could be used in conjunction with "pop-up" type dialog boxes that report the quantitative metric information to the clinician.

Also, all of the quantitative metric presentation approaches described above can be applied to three dimensional or even greater dimensional datasets.

A description will now be provided of one example of a workstation and the various menus available to an operator in order to select which metrics are to be calculated and are to appear on a mammogram image, according to an embodiment of the invention. This example is illustrative, and one of skill in the art will recognize that different types of menu screens may be implemented with the present invention, while remaining within the scope of the present invention.

A workstation that may be utilized in the present invention is shown in FIG. 6. The workstation 620 includes an image scanner/digitizer 680 for receiving a mammogram image 610. The workstation 620 also includes a processor 655 that receives the digitized mammogram image from the image scanner/digitizer 680. The processor 655 is coupled to an internal memory 665 and an external memory 675, whereby computer programs related to computing various mammogram metrics as discussed above are stored in one or both of these memories. As explained earlier, the workstation according to FIG. 6 accepts either analog mammographic images or digitized mammographic images, whereby the scanner/digitizer 680 scans and digitizes an analog mammographic image inputted thereto, and whereby the scanner/digitizer passes through (to the processor 655) and does not scan or digitize an already-digitized mammographic image that is inputted thereto.

The processor 655 is also coupled to a speaker 670, which is used for the voice-assisted features (if so desired by a clinician). The processor 655 is coupled to provide video output to a primary monitor 650, which is used to display the mammogram image. The processor 655 is also coupled to provide video output to a secondary monitor 660, which may be used to display part or all of the metrics that the clinician wants to have calculated for a mammogram image. Of course, just one monitor may be utilized in an alternative configuration.

Figure 7:
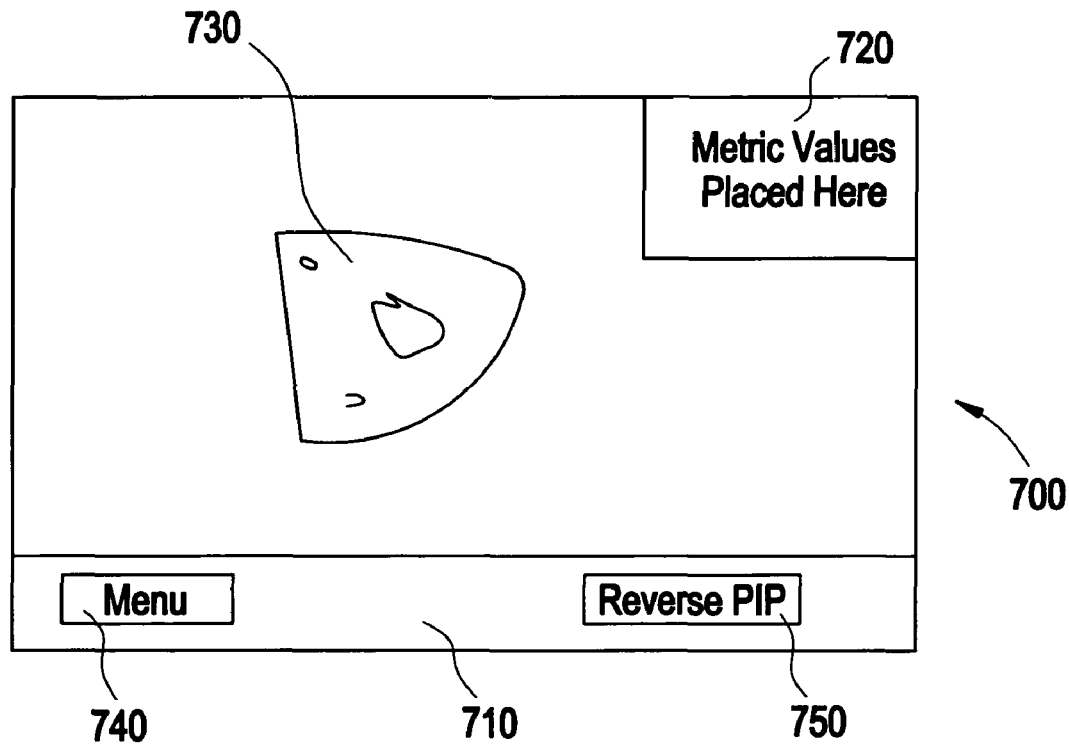
FIG. 7 is a diagram of a workstation monitor screen that provides information to a clinician, in accordance with an embodiment of the invention.

In FIG. 7, which shows a workstation display 700 (which may be a display of the primary monitor 650 of FIG. 6, for example), a global metric describing the percent glandular composition of the breast is displayed in a top right corner 720 of the workstation display 700. The placement of the metrics information is based on the clinician's preference, and may be modified based on the clinician's selections made by way of a display menu that is made available to the clinician. The menus described herein are just one example of how metrics may be displayed on a mammographic image, and they are provided by way of example and not by way of limitation. It is understood that there may be several standard configuration options, as well as a "freely configurable" option or options, with regards to metrics to be computed and presented to a clinician by way of a workstation of computer according to an embodiment of the present invention. Further, the menus may be provided to the clinician using speech synthesis software, in an alternative configuration. Also shown in FIG. 7 is a lower portion 710 of the display 700 that is dedicated to providing a "Menu" button and a "Reverse Picture-In-Picture (PIP)" button. In this configuration, the lower portion 710 of the display 700 always appears on the display 700, whereby the clinician can perform operations to return to a setup menu that allows the clinician to make any changes with respect to metrics to be calculated and the manner in which the calculated metrics are to appear on the display 700.

For example, the present invention may also allow the clinician to perform a specific "hot key" operation (hitting the "control" and "6" buttons on the computer keyboard at the same time, for example), in order to get to the initial "Menu" screen. This can be done as an alternative to performing an operation in the bottom portion 710 of the display 700.

FIG. 1 shows an initial menu screen 110 that may be utilized in the present invention. This menu screen 110 appears on the workstation display, such as the display of the primary monitor 650 shown in FIG. 6. In one implementation, the menu screen 110 appears after an initial booting up operation of the workstation 620 of FIG. 6, to allow the clinician to provide his/her inputs in order to get a desired set of metrics to be calculated and to appear on a mammogram image, to be used by the clinician for screen and diagnosis purposes. In one possible configuration, the menu screen 110 of FIG. 1 may also be obtained by the clinician pressing a particular hot key combination (see above) or by enabling the "Menu" button on the bottom portion 710 of the screen shown in FIG. 7.

Referring back to FIG. 1, the clinician selects which metrics, from a set of metrics that are capable of being calculated by the workstation according to the invention, to be calculated for a particular mammogram that the clinician wants to be analyzed by the workstation.

In FIG. 1, the clinician has selected the "Microcalcifications" metrics and the "Percent Glandular Distribution" metrics that he/she wants to be calculated for a mammogram image and which he/she wants to be provided on a workstation display. The image on the display screen can be provided in hard copy form by way of the clinician performing a print operation, whereby a printout to a printer communicatively coupled to the workstation or personal computer according to the invention will occur. For other purposes, it may also be useful to archive the metrics the radiologist used to screen or diagnose a patient breast. This archival can be accomplished by writing to computer memory a list of the quantitative metrics, their associated values, and the form in which they were presented.

When the clinician clicks the mouse on the "Next" button shown in FIG. 1, the menu screen 210 shown in FIG. 2 appears on the workstation display. The menu screen 210 allows the clinician to select how the clinician wants the first of the selected metrics (in this case, "Microcalcifications") to appear on the workstation display. The clinician has selected "Voice Assisted" for the Microcalcifications metrics, along with "Geometric Shapes". When the menu screen 210 has been completed by the clinician, he/she can either select the "Back" button to go back to the previous menu screen (in this case, menu screen 110 shown in FIG. 1), or select the "Next" button to got to the next menu screen.

FIG. 3 shows the menu screen that appears when the clinician selects the "Next" button of the menu display shown in FIG. 2. In FIG. 3, the clinician selects where he/she wants the microcalcification metrics to appear on the workstation display. For this case, the geometric shapes will appear on the display nearby the region of interest, and in color.

When the clinician has finished making selections on the menu screen 310 of FIG. 3, and then enables the "Next" button on the menu screen 310, the menu screen 410 of FIG. 4 will appear on the workstation display. The menu screen 410 allows the clinician to select how the clinician wants the "Percent Glandular Distribution", which was the second of the metrics selected for display by the clinician (see FIG. 1), to appear on the workstation display.

When the clinician has completed the selections on the menu screen 410 of FIG. 4, and then enables the "Next" button on the menu screen 410, the menu screen 510 of FIG. 5 will appear on the workstation display. The menu screen 510 allows the clinician to select where the clinician wants the "Percent Glandular Distribution" metrics to appear on the workstation display.

After the clinician has completed the menu selections for all of the metrics that he/she wants to be calculated for a mammogram image, the workstation will then start its computation process. For the example shown, after the clinician has completed the selections on the second (last) metrics on the menu screen 510 of FIG. 5, and then enables the "Next" button, the workstation will begin its computations of the metrics.

The menu screens shown in FIGS. 1-5 are illustrative of one way in which to allow a clinician to easily select metrics to be computed and the manner and way in which they are to appear on a workstation display along with a mammogram image. Of course, other ways of allowing the clinician to make these selections may be contemplated while remaining within the scope of the invention.

Due to the processing capabilities of a personal computer or workstation in accordance with the present invention, the metrics are calculated quickly. For example, metrics may be calculated and displayed in a manner of seconds or less, under most circumstances.

The preferred embodiments have been set forth herein for the purpose of illustration. However, this description should not be deemed to be a limitation on the scope of the invention. Accordingly, various modifications, adaptations, and alternatives may occur to one skilled in the art without departing from the scope of the claimed inventive concept. For example, the clinician may perform touch screen or mouse click operations on the mammographic display screen in order to highlight a particular area for which the clinician wants specific metrics to be calculated. Also, the computer or workstation according to the invention may be utilized with a tomosynthesis X-ray mammogram system described in U.S. patent application Ser. No. 10/063,357, entitled TOMOSYNTHESIS X-RAY MAMMOGRAM SYSTEM AND METHOD WITH AUTOMATIC DRIVE SYSTEM, to Yu Wang et al., filed on Apr. 15, 2002, which is incorporated herein in its entirety.

The invention claimed is:

1. An apparatus for use in mammographic analysis, comprising:
    a workstation that includes,
    an image receiving portion for receiving a mammographic image, for determining whether the mammographic image is in digital form, for converting the mammographic image to digital form if the mammographic image is not in digital form, and for outputting a digitized mammographic image;
    a computation portion for computing at least two metrics related to the digitized mammographic image, selected for display by an operator, wherein the at least two metrics are selected from a microcalcification metric, a glandular composition metric or a glandular distribution metric; and
    a presentation portion for presenting at least one of the operator selected metrics to the operator.

2. The apparatus according to claim 1, wherein the workstation further comprises:
    a menu that is presented to the operator by way of the presentation portion, the menu enabling the operator to select the at least two metrics from a list of metrics that are capable of being calculated by the workstation.

3. The apparatus according to claim 2, further comprising means for enabling the workstation to save preferences corresponding to mammographic image information and metrics information to be presented to the operator by way of the presentation portion.

4. The apparatus according to claim 1, wherein the presentation portion is a display that is capable of displaying the mammographic image on a first portion of the display, and displaying the selected metric on a second portion of the display.

5. The apparatus according to claim 1, wherein the presentation portion is a display that superimposes the selected metric on the mammographic image that is displayed on the display.

6. The apparatus according to claim 1, further comprising: an audio output device for audibly providing the selected metric to the operator.

7. The apparatus according to claim 1, further comprising: a memory that is configured to store at least one computer program for computing the at least two metrics and for presenting the selected metric to the operator.

8. A method for analyzing a mammographic image, comprising:
receiving, by a workstation, the mammographic image;
digitizing the mammographic image if the mammographic image is not already in digital form;
selecting at least two metrics related to the digitized mammographic image, wherein the at least two metrics are selected from a microcalcification metric, a glandular composition metric or a glandular distribution metric and wherein the at least two metrics are selected by an operator;
computing, by the workstation, the at least two metrics selected by the operator; and
presenting the operator selected at least two metrics to an operator, wherein the at least two metrics are selected for display by the operator.

9. The method according to claim 8, further comprising:
providing a menu, either on a display portion of the workstation or in an audible manner by way of the workstation, for enabling the operator to select the at least two metrics to be calculated and presented to the operator by way of the workstation.

10. The method according to claim 9, wherein the display portion is capable of displaying the mammographic image on a first portion of the display, and displaying the selected metric on a second portion of the display.

11. A computer program product operable by a workstation for use in mammographic analysis, comprising:
first program product code for receiving a mammographic image;
second program product code for converting the mammographic image to a digital mammographic image if the mammographic image is not already in digital form;
third program product code for computing at least two metrics related to the digitized mammographic image, selected for display by an operator, wherein the at least two metrics are selected from a microcalcification metric, a glandular composition metric or a glandular distribution metric; and
fourth program product code for presenting the operator selected at least two metrics to the operator, wherein the fourth program product code is configured to display the selected metric selected by the operator.

12. The computer program product according to claim 11, further comprising:
fifth program product code for displaying a menu on the display portion, the menu enabling the operator to select the at least two metrics from a list of metrics that are capable of being calculated by the workstation.

13. The computer program product according to claim 12, wherein the display portion is capable of displaying the mammographic image on a first portion of the display, and displaying the selected metric on a second portion of the display.

14. The computer program product according to claim 12, further comprising:
sixth program product code for converting the selected metric to an audible signal and for outputting the audible signal to an audio device.

15. The computer program product according to claim 12, further comprising:
sixth program product code that is stored in a memory and that computes the at least two metrics; and
seventh program product code that is stored in the memory and that presents the at least two metrics to the operator.

16. An apparatus for use in mammographic analysis, comprising:
a menu for displaying a plurality of metrics available for computation and display, the metric including a microcalcification metric, a glandular composition metric or a glandular distribution metric;
a computation portion for computing at least two metrics from a digitized mammographic image supplied thereto based upon metrics selected for display by an operator from the menu, wherein the at least two metrics are selected from a microcalcification metric, a glandular composition metric or a glandular distribution metric; and
a presentation portion for presenting values representative of the operator selected at least two metrics to an operator, wherein the at least two metrics selected for display by the operator.

17. The apparatus according to claim 16, wherein the presentation portion presents the at least two metrics to the operator by at least one of an audio display and a visual display.

18. An apparatus for use in mammographic image analysis, comprising:
means for displaying a plurality of metrics available for computation and display, the metrics including a microcalcification metric, a glandular composition metric or a glandular distribution metric;
means for receiving a mammographic image and at least two metrics obtained from the mammographic image; and
means for computing the at least two metrics from a mammographic image supplied thereto based upon metrics selected for display by an operator from the menu, wherein the at least two metrics are selected from a microcalcification metric, a glandular composition metric or a glandular distribution metric; and
means for presenting the mammographic image and the user selected at least two metrics.

19. The apparatus according to claim 18, wherein the presenting means comprises:
a first display portion for displaying the mammographic image; and
a second display portion for displaying the selected metrics.

20. The apparatus according to claim 18, wherein the presenting means comprises:
a display portion for displaying the selected metrics superimposed with the mammographic image.

21. The apparatus according to claim 18, wherein the presenting means comprises:
a display portion for displaying the selected metrics; and
an audio output portion for providing information regarding the selected metrics in audible form to the user.

* * * * *